(12) United States Patent
Ishii et al.

(10) Patent No.: US 11,819,312 B2
(45) Date of Patent: Nov. 21, 2023

(54) PHOTOACOUSTIC APPARATUS AND METHOD FOR CONTROLLING PHOTOACOUSTIC APPARATUS

(71) Applicant: FUJIFILM Corporation, Tokyo (JP)

(72) Inventors: Hiroyasu Ishii, Kanagawa (JP); Keiji Tsubota, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 697 days.

(21) Appl. No.: 16/926,938

(22) Filed: Jul. 13, 2020

(65) Prior Publication Data

US 2020/0345237 A1 Nov. 5, 2020

Related U.S. Application Data

(63) Continuation of application No. PCT/JP2019/001942, filed on Jan. 23, 2019.

(30) Foreign Application Priority Data

Mar. 5, 2018 (JP) ................................. 2018-038458

(51) Int. Cl.
*A61B 5/00* (2006.01)
*G08B 21/18* (2006.01)
(Continued)

(52) U.S. Cl.
CPC .......... *A61B 5/0095* (2013.01); *A61B 5/7246* (2013.01); *G08B 21/182* (2013.01);
(Continued)

(58) Field of Classification Search
CPC ..... A61B 5/0095; A61B 5/489; A61B 8/0891; A61B 8/5269; H01S 3/0014; H01S 3/061; H01S 3/08054; H01S 3/11; G01N 29/2418
See application file for complete search history.

(56) References Cited

U.S. PATENT DOCUMENTS

2009/0034564 A1* 2/2009 Lederer .................. H01S 3/1312
372/25
2010/0191109 A1 7/2010 Fukutani et al.
(Continued)

FOREIGN PATENT DOCUMENTS

JP 2013128759 A 7/2013
JP 2015126900 A 7/2015
(Continued)

OTHER PUBLICATIONS

International Search Report issued in PCT/JP2019/001942; dated Mar. 19, 2019.
(Continued)

*Primary Examiner* — Boniface Ngathi
(74) *Attorney, Agent, or Firm* — Studebaker & Brackett PC

(57) ABSTRACT

A photoacoustic apparatus includes a laser light irradiating unit that irradiates an inside of a subject with pulsed light; a photoacoustic signal acquiring unit that acquires a photoacoustic signal from a photoacoustic wave from the subject; a light amount detecting unit that detects a light amount of the pulsed light; a correlation data memory that stores first correlation data and second correlation data; an energy estimating unit that estimates an energy on the basis of the amount of the pulsed light and the first correlation data; a pulse width estimating unit that estimates a pulse width on the basis of the estimated energy and the second correlation data; and a photoacoustic signal correcting unit that corrects the photoacoustic signal on the basis of a first difference between the estimated energy and a reference energy and a second difference between the estimated pulse width and a reference pulse width.

19 Claims, 13 Drawing Sheets

(51) Int. Cl.
    *G08B 5/22*      (2006.01)
    *H01S 3/00*      (2006.01)
    *H01S 3/06*      (2006.01)
    *H01S 3/08*      (2023.01)

(52) U.S. Cl.
    CPC ............. *G08B 5/22* (2013.01); *H01S 3/0014* (2013.01); *H01S 3/061* (2013.01); *H01S 3/08054* (2013.01)

(56) References Cited

U.S. PATENT DOCUMENTS

| | | |
|---|---|---|
| 2016/0058290 A1 | 3/2016 | Nakatsuka et al. |
| 2016/0150967 A1 | 6/2016 | Nakajima et al. |
| 2017/0215804 A1* | 8/2017 | Miyasato ............. A61B 5/0073 |

FOREIGN PATENT DOCUMENTS

| | | |
|---|---|---|
| JP | 2016047232 A | 4/2016 |
| JP | 2016101369 A | 6/2016 |
| WO | 2010024290 A1 | 3/2010 |

OTHER PUBLICATIONS

International Preliminary Report on Patentability and Written Opinion issued in PCT/JR2019/001942; dated Sep. 8, 2020.

* cited by examiner

PHOTOACOUSTIC APPARATUS AND METHOD FOR CONTROLLING PHOTOACOUSTIC APPARATUS

CROSS-REFERENCE TO RELATED APPLICATIONS

This application is a Continuation of PCT International Application No. PCT/JP2019/001942 filed on Jan. 23, 2019, which claims priority under 35 U.S.C. § 119(a) to Japanese Patent Application No. 2018-038458 filed on Mar. 5, 2018. Each of the above application(s) is hereby expressly incorporated by reference, in its entirety, into the present application.

BACKGROUND OF THE INVENTION

1. Field of the Invention

The present invention relates to a photoacoustic apparatus and a method for controlling the photoacoustic apparatus, and specifically relates to a photoacoustic apparatus that corrects a photoacoustic signal and a method for controlling the photoacoustic apparatus.

2. Description of the Related Art

Hitherto, a photoacoustic apparatus has been known as an apparatus that acquires an image of the inside of a subject by using a photoacoustic wave. Typically, a photoacoustic apparatus irradiates the inside of a subject with pulsed laser light emitted by a laser light source and receives, using an array transducer having a plurality of vibrators arranged, a photoacoustic wave emitted from substance in the living body of the subject, such as hemoglobin, thereby acquiring a photoacoustic signal. Furthermore, the photoacoustic apparatus is capable of electrically processing the acquired photoacoustic signal to generate an image of the inside of the subject.

Regarding such a photoacoustic apparatus, it has generally been known that a laser light source changes, for example, degrades, as time elapses. Thus, various measures have been taken to prevent an acquired photoacoustic signal from being changed in accordance with a chronological change in the laser light source.

For example, JP2015-126900A discloses a photoacoustic apparatus that measures the light amount value of pulsed laser light emitted by a laser light source and corrects the intensity of a photoacoustic signal on the basis of the measured light amount value.

In addition, JP2013-128759A discloses a photoacoustic apparatus that estimates the pulse width of pulsed laser light emitted by a laser light source on the basis of emission conditions of pulsed laser light, such as the excitation energy and emission frequency of the pulsed laser light, and corrects a photoacoustic signal on the basis of the estimated pulse width.

SUMMARY OF THE INVENTION

In the photoacoustic apparatus disclosed in JP2015-126900A, the intensity of a photoacoustic signal is corrected on the basis of only the light amount value of pulsed laser light emitted by the laser light source, but the pulse width of the pulsed laser light is not considered. Thus, the intensity of a photoacoustic signal may be significantly changed in accordance with a chronological change in the laser light source.

In the photoacoustic apparatus disclosed in JP2013-128759A, a photoacoustic signal is corrected on the basis of the pulse width of pulsed laser light estimated on the basis of emission conditions, such as the excitation energy and emission frequency of the pulsed laser light, without measuring the pulse width of pulsed laser light emitted by the laser light source as appropriate. Thus, a difference may occur between the pulse width estimated on the basis of emission conditions and the pulse width of pulsed laser light actually output from the laser light source. Accordingly, the intensity of a photoacoustic signal may be significantly changed in accordance with a chronological change in the laser light source.

The present invention has been made to solve these conventional issues, and an object of the present invention is to provide a photoacoustic apparatus capable of reducing an influence of a chronological change in a laser light source on a photoacoustic signal and a method for controlling the photoacoustic apparatus.

To achieve the above object, a photoacoustic apparatus according to the present invention includes a laser light source that emits pulsed laser light; a laser light irradiating unit that irradiates an inside of a subject with the pulsed laser light to cause a photoacoustic wave to be emitted from tissue of the subject; a photoacoustic signal acquiring unit that receives the photoacoustic wave emitted from the tissue of the subject and acquires a photoacoustic signal; a light amount detecting unit that detects a light amount of the pulsed laser light emitted by the laser light source; a correlation data memory that stores first correlation data and second correlation data, the first correlation data representing a relationship between a light amount detected by the light amount detecting unit and an energy of the pulsed laser light, the second correlation data representing a relationship between an energy of the pulsed laser light and a pulse width of the pulsed laser light; an energy estimating unit that estimates an energy of the pulsed laser light by using the first correlation data on the basis of the light amount detected by the light amount detecting unit; a pulse width estimating unit that estimates a pulse width of the pulsed laser light by using the second correlation data on the basis of the energy of the pulsed laser light estimated by the energy estimating unit; a photoacoustic signal correcting unit that corrects the photoacoustic signal acquired by the photoacoustic signal acquiring unit on the basis of both a first difference between the energy of the pulsed laser light estimated by the energy estimating unit and a determined reference energy and a second difference between the pulse width of the pulsed laser light estimated by the pulse width estimating unit and a determined reference pulse width; and a photoacoustic image generating unit that generates a photoacoustic image from the photoacoustic signal corrected by the photoacoustic signal correcting unit.

Preferably, the photoacoustic signal correcting unit includes a first difference calculating unit that calculates the first difference on the basis of the energy of the pulsed laser light estimated by the energy estimating unit and the determined reference energy, a second difference calculating unit that calculates the second difference on the basis of the pulse width of the pulsed laser light estimated by the pulse width estimating unit and the determined reference pulse width, and a correction executing unit that corrects the photoacoustic signal in accordance with the first difference calculated by the first difference calculating unit and further corrects the photoacoustic signal in accordance with the second difference calculated by the second difference calculating unit.

Furthermore, the correlation data memory may store third correlation data and fourth correlation data, the third correlation data representing a relationship between an energy of the pulsed laser light and the photoacoustic signal acquired by the photoacoustic signal acquiring unit, the fourth correlation data representing a relationship between a pulse width of the pulsed laser light and the photoacoustic signal acquired by the photoacoustic signal acquiring unit. The correction executing unit may correct the photoacoustic signal on the basis of the first difference and the third correlation data and may further correct the photoacoustic signal on the basis of the second difference and the fourth correlation data.

In addition, the laser light source may emit pulsed laser light beams having a respective plurality of wavelengths. The photoacoustic signal acquiring unit may acquire, for each wavelength, the photoacoustic signal. The correlation data memory may store, for each wavelength, the first correlation data and the second correlation data corresponding to the wavelength. The energy estimating unit may estimate, for each wavelength, an energy of the pulsed laser light beam. The pulse width estimating unit may estimate, for each wavelength, a pulse width of the pulsed laser light beam. The photoacoustic signal correcting unit may correct, for each wavelength, the photoacoustic signal. The photoacoustic image generating unit may generate, for each wavelength, the photoacoustic image.

Furthermore, the light amount detecting unit may include a single light amount detecting unit that detects amounts of the pulsed laser light beams having the respective plurality of wavelengths.

Alternatively, the light amount detecting unit may include a plurality of light amount detecting units each of which detects an amount of one of the pulsed laser light beams having the respective plurality of wavelengths.

In addition, the photoacoustic image generating unit may generate an image about a characteristic distribution in a living body or an image about a living tissue distribution.

In addition, the light amount detecting unit may include a photodetector and either an integration circuit or a peak hold circuit, the integration circuit computing an integral of electric charge of an optical signal detected by the photodetector, the peak hold circuit measuring a crest value of the optical signal.

Furthermore, the photodetector may be formed of any one of a photodiode, a phototransistor, or a phototube.

Furthermore, the photodetector may detect either a part of light branched off from an optical path of the pulsed laser light emitted by the laser light source or scattered light of the pulsed laser light emitted by the laser light source.

In addition, the photodetector may be disposed inside a resonator of the laser light source.

In addition, the photoacoustic apparatus may further include a warning unit that monitors at least one of an amount of temporal change in the energy of the pulsed laser light estimated by the energy estimating unit or an amount of temporal change in the pulse width of the pulsed laser light estimated by the pulse width estimating unit and that issues a warning in a case where the amount of temporal change that is being monitored exceeds an upper limit value determined for the energy of the pulsed laser light or an upper limit value determined for the pulse width of the pulsed laser light.

The photoacoustic apparatus may further include a pulsed laser light emission stopping unit that stops emission of the pulsed laser light from the laser light source in a case where at least one of the energy of the pulsed laser light estimated by the energy estimating unit or the pulse width of the pulsed laser light estimated by the pulse width estimating unit is out of a guarantee range determined for the energy of the pulsed laser light or a guarantee range determined for the pulse width of the pulsed laser light.

A method for controlling a photoacoustic apparatus according to the present invention includes irradiating an inside of a subject with pulsed laser light emitted by a laser light source to cause a photoacoustic wave to be emitted from tissue of the subject; receiving the photoacoustic wave emitted from the tissue of the subject and acquiring a photoacoustic signal; detecting a light amount of the pulsed laser light emitted by the laser light source; estimating an energy of the pulsed laser light by using first correlation data on the basis of a detected amount of the pulsed laser light, the first correlation data representing a relationship between an amount of the pulsed laser light emitted by the laser light source and an energy of the pulsed laser light; estimating a pulse width of the pulsed laser light by using second correlation data on the basis of the estimated energy of the pulsed laser light, the second correlation data representing a relationship between an energy of the pulsed laser light and a pulse width of the pulsed laser light; correcting the photoacoustic signal on the basis of both a first difference between the estimated energy of the pulsed laser light and a determined reference energy and a second difference between the estimated pulse width of the pulsed laser light and a determined reference pulse width; and generating a photoacoustic image from the corrected photoacoustic signal.

According to the present invention, a photoacoustic apparatus includes a correlation data memory that stores first correlation data and second correlation data, the first correlation data representing a relationship between an amount and energy of pulsed laser light emitted by a laser light source, the second correlation data representing a relationship between an energy and pulse width of the pulsed laser light; an energy estimating unit that estimates an energy of the pulsed laser light by using the first correlation data on the basis of a light amount of pulsed laser light detected by a light amount detecting unit; a pulse width estimating unit that estimates a pulse width of the pulsed laser light by using the second correlation data on the basis of the energy of the pulsed laser light estimated by the energy estimating unit; and a photoacoustic signal correcting unit that corrects a photoacoustic signal acquired by a photoacoustic signal acquiring unit on the basis of both a first difference between the energy of the pulsed laser light estimated by the energy estimating unit and a determined reference energy and a second difference between the pulse width of the pulsed laser light estimated by the pulse width estimating unit and a determined reference pulse width. Thus, it is possible to reduce an influence of a chronological change in the laser light source on a photoacoustic signal.

DESCRIPTION OF THE PREFERRED EMBODIMENTS

Hereinafter, embodiments of the present invention will be described with reference to the attached drawings.

First Embodiment

Figure 1:
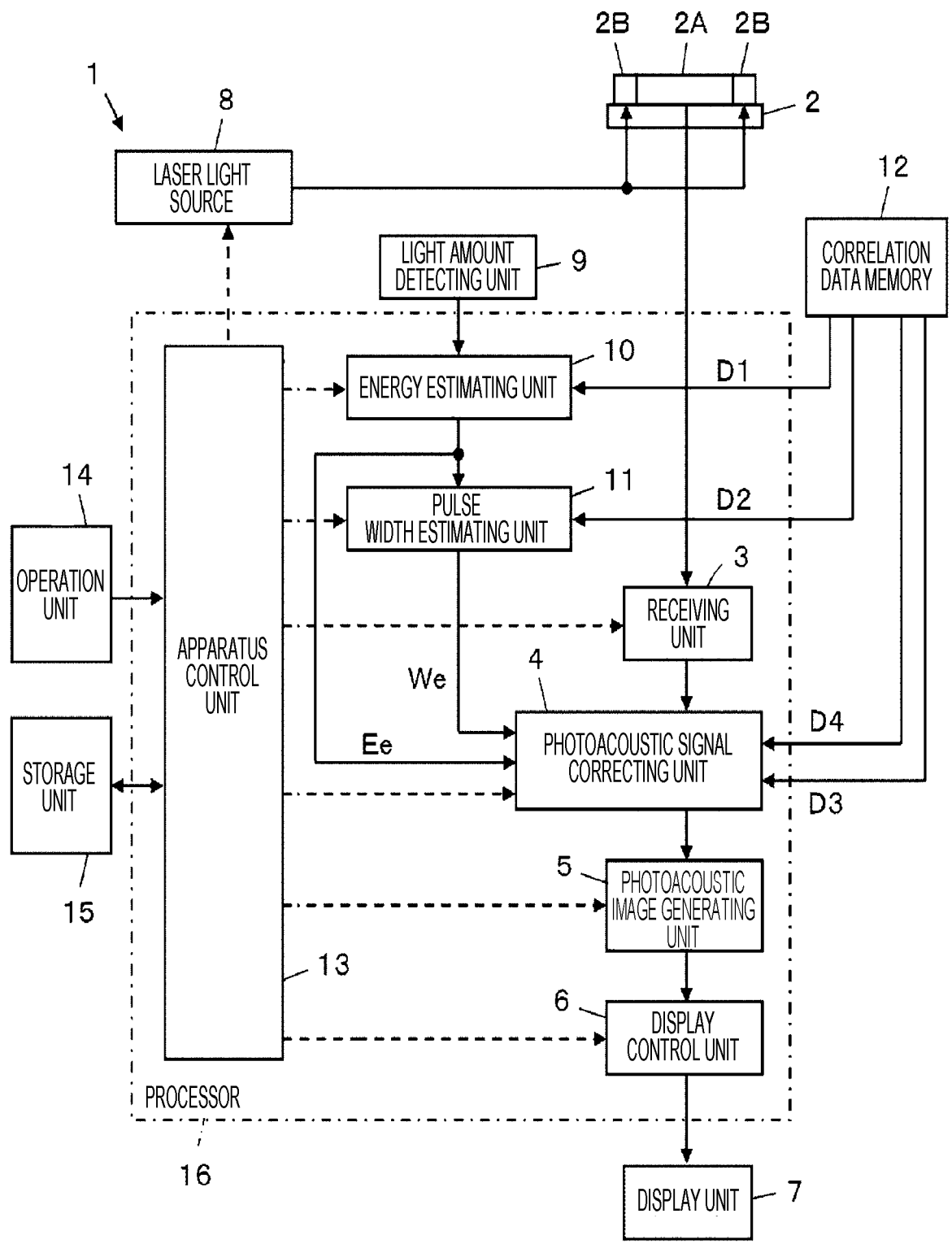
FIG. 1 is a block diagram illustrating the configuration of a photoacoustic apparatus according to a first embodiment of the present invention.

FIG. 1 illustrates the configuration of a photoacoustic apparatus 1 according to a first embodiment of the present invention. As illustrated in FIG. 1, the photoacoustic apparatus 1 includes a probe 2 including an array transducer 2A and a laser light irradiating unit 2B. A receiving unit 3, a photoacoustic signal correcting unit 4, a photoacoustic image generating unit 5, a display control unit 6, and a display unit 7 are connected to the array transducer 2A in order. In addition, a laser light source 8 is connected to the laser light irradiating unit 2B. In addition, the photoacoustic apparatus 1 includes a light amount detecting unit 9 near an optical path of laser light emitted by the laser light source 8, and an energy estimating unit 10 is connected to the light amount detecting unit 9. A pulse width estimating unit 11 is connected to the energy estimating unit 10, and both the energy estimating unit 10 and the pulse width estimating unit 11 are connected to the photoacoustic signal correcting unit 4. In addition, a correlation data memory 12 is connected to each of the photoacoustic signal correcting unit 4, the energy estimating unit 10, and the pulse width estimating unit 11.

Furthermore, an apparatus control unit 13 is connected to the receiving unit 3, the photoacoustic signal correcting unit 4, the photoacoustic image generating unit 5, the display control unit 6, the laser light source 8, the energy estimating unit 10, and the pulse width estimating unit 11, and an operation unit 14 and a storage unit 15 are connected to the apparatus control unit 13. The apparatus control unit 13 and the storage unit 15 are connected to each other so as to be capable of bidirectional transmission/reception of information.

In addition, the receiving unit 3, the photoacoustic signal correcting unit 4, the photoacoustic image generating unit 5, the display control unit 6, the energy estimating unit 10, the pulse width estimating unit 11, and the apparatus control unit 13 constitute a processor 16. Although not illustrated, the array transducer 2A of the probe 2 and the receiving unit 3 constitute a photoacoustic signal acquiring unit.

Figure 2:
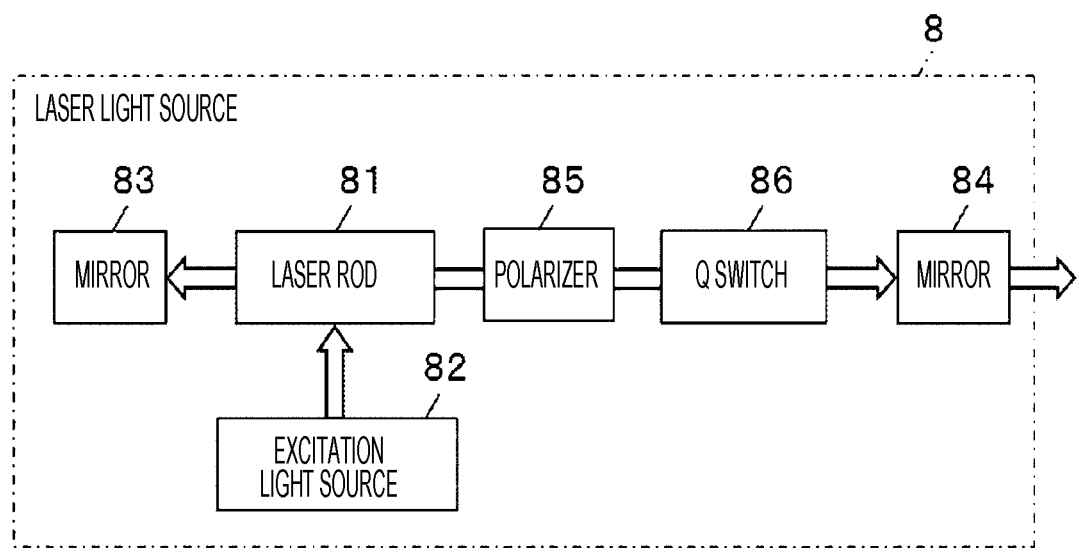
FIG. 2 is a block diagram illustrating an internal configuration of a laser light source according to the first embodiment of the present invention.

The laser light source 8 of the photoacoustic apparatus 1 emits pulsed laser light under control by the apparatus control unit 13. As illustrated in FIG. 2, the laser light source 8 has a laser rod 81, an excitation light source 82, a mirror 83, a mirror 84, a polarizer 85, and a Q switch 86. The laser rod 81 is a laser medium. For example, an alexandrite crystal, a Nd:YAG crystal, or the like may be used for the laser rod 81. The excitation light source 82 is a light source that irradiates the laser rod 81 with excitation light. For example, a light source such as a flash lamp or a laser diode may be used as the excitation light source 82.

The mirrors 83 and 84 face each other with the laser rod 81 interposed therebetween. The mirrors 83 and 84 constitute an optical resonator. In this optical resonator, the mirror 84 is on the output side. The polarizer 85 and the Q switch 86 are inserted into the optical resonator. The Q switch 86 causes a quick change from a state where optical loss in the optical resonator is large to a state where optical loss is small, and thereby pulsed laser light can be acquired. The pulsed laser light emitted from the mirror 84 on the output side of the laser light source 8 is guided to the laser light irradiating unit 2B of the probe 2 via a light guide member or the like that is not illustrated.

The laser light irradiating unit 2B of the probe 2 is disposed at both ends of the array transducer 2A, and irradiates the inside of a subject with pulsed laser light guided from the laser light source 8 via the light guide member or the like that is not illustrated, while being in contact with a body surface of the subject. The pulsed laser light applied to the inside of the subject in this manner is absorbed as thermal energy by substance in the living body of the subject, such as hemoglobin. The substance in the living body that has absorbed the pulsed laser light expands and contracts, thereby emitting a photoacoustic wave.

The array transducer 2A of the probe 2 illustrated in FIG. 1 has a plurality of ultrasonic vibrators arranged in a one-dimensional or two-dimensional manner. These ultrasonic vibrators receive a photoacoustic wave generated by irradiating, by the laser light irradiating unit 2B, the inside of a subject with pulsed laser light from the laser light source 8, and output reception signals to the receiving unit 3.

The plurality of ultrasonic vibrators constituting the array transducer 2A are each constituted by forming electrodes at both ends of a piezoelectric body made of, for example, a piezoelectric ceramic such as lead zirconate titanate (PZT), a polymer piezoelectric element such as poly vinylidene difluoride (PVDF), or a piezoelectric single crystal such as lead magnesium niobate-lead titanate solid solution (PMN-PT).

Figure 3:
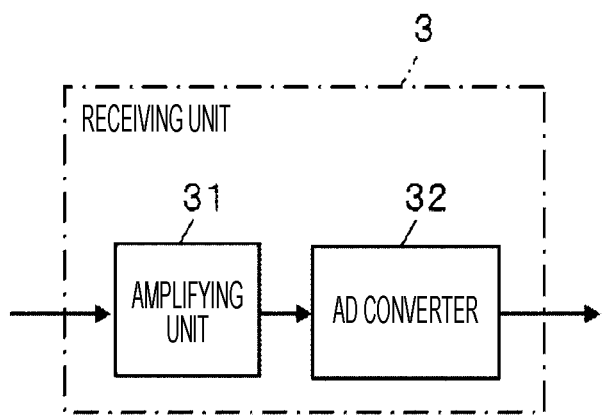
FIG. 3 is a block diagram illustrating an internal configuration of a receiving unit according to the first embodiment of the present invention.

The receiving unit 3 of the processor 16 processes reception signals output from the array transducer 2A of the probe 2 in accordance with a control signal from the apparatus control unit 13. As illustrates in FIG. 3, the receiving unit 3 has a configuration in which an amplifying unit 31 and an analog-to-digital (AD) converter 32 are connected in series to each other. The amplifying unit 31 amplifies reception signals received from the individual ultrasonic vibrators constituting the array transducer 2A and transmits the amplified reception signals to the AD converter 32. The AD converter 32 converts the reception signals received from the amplifying unit 31 into digital data and transmits the digital data to the photoacoustic signal correcting unit 4 of the processor 16.

Figure 4:
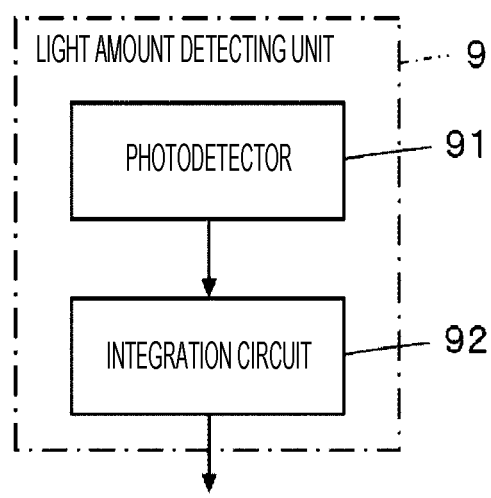
FIG. 4 is a block diagram illustrating an internal configuration of a light amount detecting unit according to the first embodiment of the present invention.

The light amount detecting unit 9 of the photoacoustic apparatus 1 measures (monitors) at least a part of pulsed laser light emitted by the laser light source 8 and detects the light amount thereof. As illustrated in FIG. 4, the light amount detecting unit 9 has a configuration in which a photodetector 91 and an integration circuit 92 are connected in series to each other. The photodetector 91 is disposed near the optical path of the pulsed laser light emitted by the laser light source 8 and detects a part of the pulsed laser light as an optical signal, which is an electric signal. As the photodetector 91, for example, a phototube such as a photomultiplier tube, a photodiode, a phototransistor, or the like is used. For example, a half mirror that is not illustrated is disposed in the optical path of the pulsed laser light emitted by the laser light source 8, and the photodetector 91 is capable of detecting a part of pulsed laser light branched off by the half mirror. Alternatively, the photodetector 91 may detect, for example, scattered light of the pulsed laser light emitted by the laser light source 8.

The integration circuit 92 of the light amount detecting unit 9 calculates an integral of electric charge of an optical signal detected by the photodetector 91 and AD converts the integral into digital data, thereby acquiring the light amount of pulsed laser light. The photodetector 91 detects a part of pulsed laser light branched off by the half mirror or scattered light of pulsed laser light, and considers the reflectance of the half mirror, the ratio of the amount of scattered light to the amount of pulsed laser light, and so forth, thereby being capable of acquiring the light amount of pulsed laser light emitted by the laser light source 8.

The correlation data memory 12 of the photoacoustic apparatus 1 stores first correlation data D1 representing a relationship between the light amount of pulsed laser light emitted by the laser light source 8 and the energy of the pulsed laser light, second correlation data D2 representing a relationship between the energy of the pulsed laser light and the pulse width of the pulsed laser light, third correlation data D3 representing a relationship between the energy of the pulsed laser light and a photoacoustic signal acquired by the receiving unit 3, and fourth correlation data D4 representing a relationship between the pulse width of the pulsed laser light and a photoacoustic signal acquired by the receiving unit 3. Here, as the pulse width of the pulsed laser light, for example, the half-width or 1/10-width of the waveform of one pulse of the pulsed laser light emitted by the laser light source 8 may be used. The first correlation data D1, the second correlation data D2, the third correlation data D3, and the fourth correlation data D4 are created by measuring in advance the amount, energy, and pulse width of pulsed laser light and a photoacoustic signal based on the pulsed laser light.

Here, as the correlation data memory 12, a recording medium such as a hard disc drive (HDD), a solid state drive (SSD), a flexible disc (FD), a magneto-optical disc (MO disc), magnetic tape (MT), a random access memory (RAM), a compact disc (CD), a digital versatile disc (DVD), a secure digital card (SD card), or a universal serial bus memory (USB memory), a server, or the like may be used.

The energy estimating unit 10 of the processor 16 estimates an energy Ee of the pulsed laser light emitted by the laser light source 8 on the basis of the light amount of pulsed laser light detected by the light amount detecting unit 9 and the first correlation data D1 stored in the correlation data memory 12.

The pulse width estimating unit 11 of the processor 16 estimates a pulse width We of the pulsed laser light emitted by the laser light source 8 on the basis of the energy Ee of the pulsed laser light estimated by the energy estimating unit 10 and the second correlation data D2 stored in the correlation data memory 12.

Figure 5:
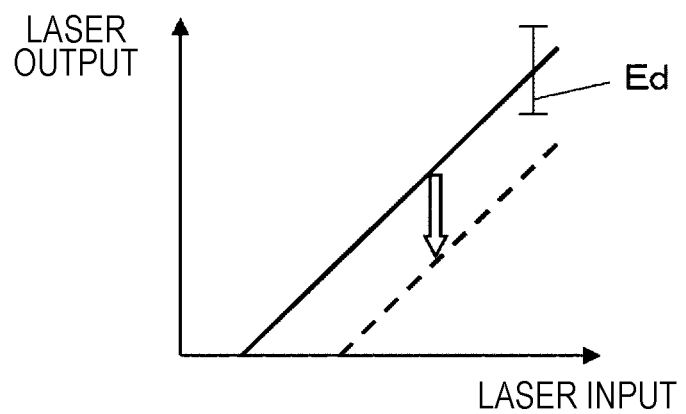
FIG. 5 is a diagram schematically illustrating a relationship between an energy input to the laser light source and an energy of pulsed laser light output from the laser light source.

In general, use of a laser light source for a certain period may cause degradation of an excitation light source, a laser rod, and so forth. In this case, for example, the energy of outgoing pulsed laser light may decrease relative to the energy input to the laser light source, as illustrated in FIG. 5. Such a decrease in the energy of outgoing pulsed laser light may decrease the thermal energy absorbed by substance in a living body irradiated with the pulsed laser light in a subject, and as a result the intensity of a photoacoustic wave emitted from the substance in the living body may decrease. Actually, even in a case where constant energy is input to the laser light source, the energy of pulsed laser light output from the laser light source has a variation Ed among individual pulses. Because of the variation Ed in the energy of pulsed laser light, the intensity of a photoacoustic signal acquired on the basis of the pulsed laser light emitted by the laser light source often fluctuates from an ideal value for the energy input to the laser light source.

Figure 6:
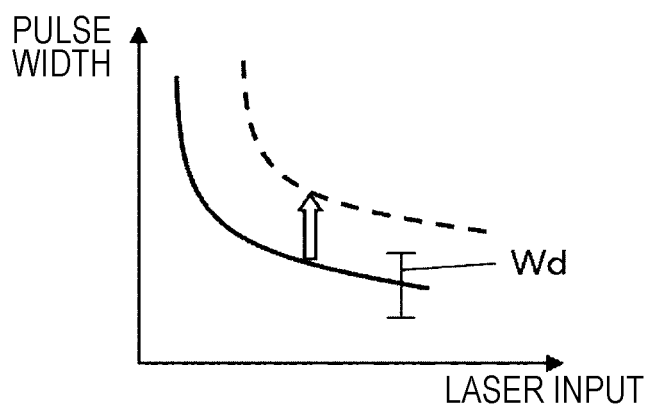
FIG. 6 is a diagram schematically illustrating a relationship between an energy input to the laser light source and a pulse width of pulsed laser light output from the laser light source.

Furthermore, in a case where the laser light source degrades, the pulse width of outgoing pulsed laser light may increase relative to the energy input to the laser light source, as illustrated in FIG. 6. Such an increase in the pulse width of outgoing pulsed laser light decreases the thermal energy absorbed by substance in the living body of the subject per unit time. Thus, a temporal cycle of expansion and contraction of the substance in the living body may become longer, and the frequency of a photoacoustic wave emitted from the substance in the living body may increase. In such a case, the range of a photoacoustic wave emitted from the substance in the living body is far from the reception range of the array transducer 2A, and thus the intensity of a reception signal acquired by the array transducer 2A may decrease. In addition, similarly to the energy of pulsed laser light, the pulse width of pulsed laser light has a variation Wd among individual pulses. Because of the variation Wd in the pulse width of pulsed laser light, the intensity of a photoacoustic signal acquired on the basis of pulsed laser light emitted by the laser light source often fluctuates from an ideal value for the energy input to the laser light source.

Figure 7:
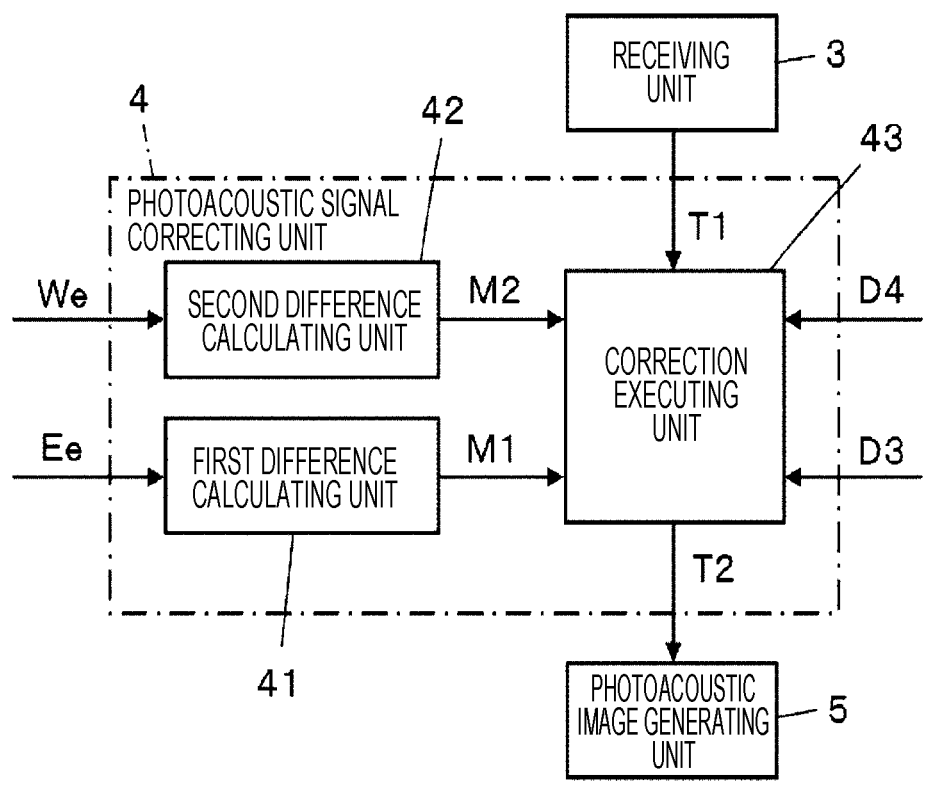
FIG. 7 is a block diagram illustrating an internal configuration of a photoacoustic signal correcting unit according to the first embodiment of the present invention.

The photoacoustic signal correcting unit 4 of the processor 16 corrects a photoacoustic signal acquired by the receiving unit 3 on the basis of the energy Ee calculated by the energy estimating unit 10 and the pulse width We calculated by the pulse width estimating unit 11, to suppress a change in the photoacoustic signal caused by a chronological change in the laser light source 8. As illustrated in FIG. 7, the photoacoustic signal correcting unit 4 of the processor 16 has a first difference calculating unit 41, a second difference calculating unit 42, and a correction executing unit 43. The first difference calculating unit 41 and the second difference calculating unit 42 are each connected to the correction executing unit 43.

The first difference calculating unit 41 of the photoacoustic signal correcting unit 4 receives the value of the energy Ee from the energy estimating unit 10, calculates a first difference M1 between the energy Ee and a determined reference energy, and transmits the first difference M1 to the correction executing unit 43. Also, the second difference calculating unit 42 of the photoacoustic signal correcting unit 4 receives the value of the pulse width We from the pulse width estimating unit 11, calculates a second difference M2 between the pulse width We and a determined reference pulse width, and transmits the second difference M2 to the correction executing unit 43.

The correction executing unit 43 of the photoacoustic signal correcting unit 4 corrects a photoacoustic signal T1 acquired by the receiving unit 3 on the basis of both the first difference M1 received from the first difference calculating unit 41 and the second difference M2 received from the second difference calculating unit 42, and transmits a corrected photoacoustic signal T2 to the photoacoustic image generating unit 5. In this case, the correction executing unit 43 performs photoacoustic signal correction that is based on the first difference M1 and the third correlation data D3 stored in the correlation data memory 12 and photoacoustic signal correction that is based on the second difference M2 and the fourth correlation data D4 stored in the correlation data memory 12.

Figure 8:
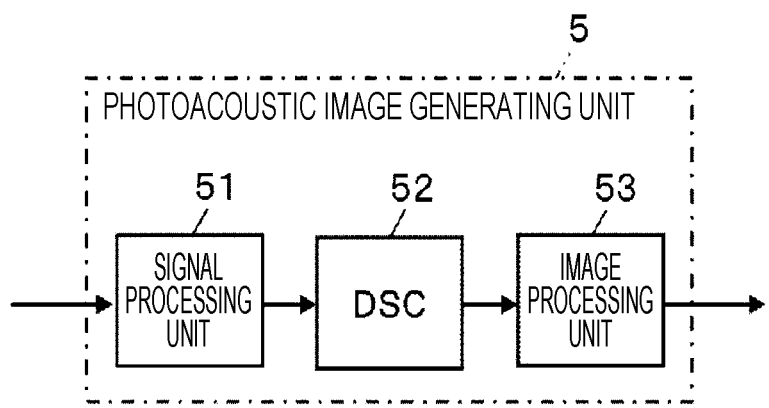
FIG. 8 is a block diagram illustrating an internal configuration of a photoacoustic image generating unit according to the first embodiment of the present invention.

As illustrated in FIG. 8, the photoacoustic image generating unit 5 of the processor 16 has a configuration in which a signal processing unit 51, a digital scan converter (DSC) 52, and an image processing unit 53 are connected in series to each other. The signal processing unit 51 performs reception focus processing, in which individual pieces of data of a reception signal are added by applying respective delays (phasing addition) on the basis of a reception delay pattern selected in accordance with a control signal from the apparatus control unit 13. The reception focus processing generates a sound ray signal in which the focus of a photoacoustic wave converges to one scan line. In addition, the signal processing unit 51 performs, on the generated sound ray signal, correction of attenuation resulting from a propagation distance in accordance with the depth of the position at which the photoacoustic wave was emitted, and then performs envelope detection processing thereon, thereby generating a B-mode image signal. The B-mode image signal generated in this manner is output to the DSC 52.

The DSC 52 of the photoacoustic image generating unit 5 performs raster conversion on the B-mode image signal to generate an image signal conforming to the scanning scheme of an ordinary television signal. The image processing unit 53 of the photoacoustic image generating unit 5 performs various necessary image processing operations, such as brightness correction, gradation correction, sharpness correction, and color correction, on the image data acquired in the DSC 52, and outputs the B-mode image signal to the display control unit 6.

The apparatus control unit 13 of the processor 16 controls the individual units of the photoacoustic apparatus 1 on the basis of a program stored in the storage unit 15 or the like in advance and a user operation performed via the operation unit 14.

The display control unit 6 of the processor 16 performs predetermined processing on the image output from the photoacoustic image generating unit 5 to generate an image that can be displayed on the display unit 7, under control by the apparatus control unit 13.

The display unit 7 of the photoacoustic apparatus 1 displays the image generated by the display control unit 6 and includes, for example, a display device such as a liquid crystal display (LCD).

The operation unit 14 of the photoacoustic apparatus 1 is used by a user to perform an input operation and may include a keyboard, a mouse, a trackball, a touch pad, a touch panel, and the like.

The storage unit 15 stores an operation program or the like for the photoacoustic apparatus 1 and may use, like the correlation data memory 12, a recording medium such as an HDD, an SSD, an FD, an MO disc, MT, a RAM, a CD, a DVD, an SD card, or a USB memory, a server connected to a network, or the like.

The processor 16 having the receiving unit 3, the photoacoustic signal correcting unit 4, the photoacoustic image generating unit 5, the display control unit 6, the energy estimating unit 10, the pulse width estimating unit 11, and the apparatus control unit 13 is constituted by a central processing unit (CPU) and a control program for causing the CPU to execute various processing operations, but may be constituted by using a digital circuit. In addition, the receiving unit 3, the photoacoustic signal correcting unit 4, the photoacoustic image generating unit 5, the display control unit 6, the energy estimating unit 10, the pulse width estimating unit 11, and the apparatus control unit 13 may be constituted by partially or fully integrating them into one CPU.

Figure 9:
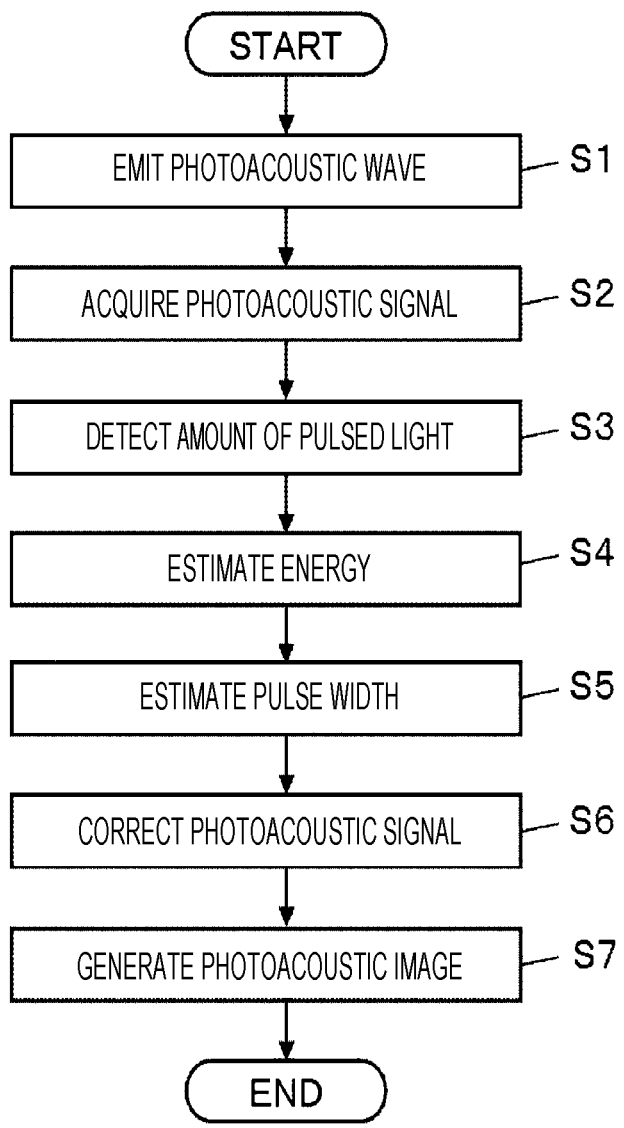
FIG. 9 is a flowchart illustrating an operation of the photoacoustic apparatus according to the first embodiment of the present invention.

Next, an operation of the photoacoustic apparatus 1 according to the first embodiment of the present invention will be described with reference to the flowchart illustrated in FIG. 9.

First, in step S1, the laser light source 8 emits pulsed laser light under control by the apparatus control unit 13. The pulsed laser light emitted by the laser light source 8 is guided by the light guide member or the like that is not illustrated, and the laser light irradiating unit 2B of the probe 2 irradiates the inside of a subject with the pulsed laser light. The irradiation of the inside of the subject with the pulsed laser light causes substance in the living body of the subject, such as hemoglobin, to absorb the pulsed laser light and emit a photoacoustic wave.

In step S2, the array transducer 2A of the probe 2 receives the photoacoustic wave emitted from the substance in the living body of the subject, and transmits a reception signal to the receiving unit 3. Accordingly, the receiving unit 3 acquires a photoacoustic signal.

In the following step S3, the light amount detecting unit 9 detects the light amount of at least a part of the pulsed laser light emitted by the laser light source 8.

Figure 10:
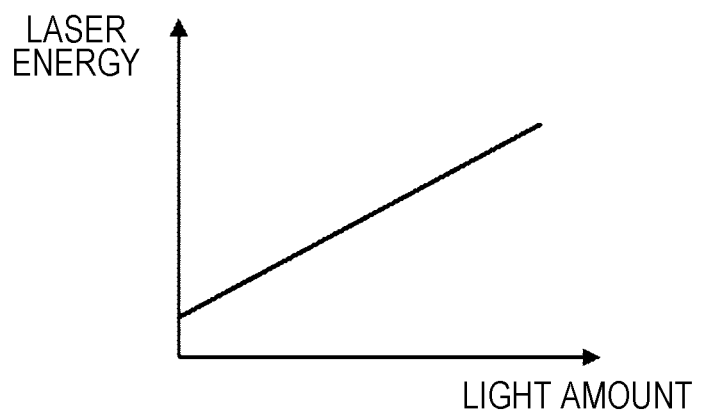
FIG. 10 is a diagram schematically illustrating a correlation between a light amount value and energy of pulsed laser light output from the laser light source.

In step S4, the energy estimating unit 10 estimates the energy of the pulsed laser light on the basis of the light amount detected in step S3 and the first correlation data D1 stored in the correlation data memory 12. Here, the first correlation data D1 is data representing a relationship between the light amount and energy of at least a part of pulsed laser light emitted by the laser light source 8 as illustrated in FIG. 10, for example. The energy estimating unit 10 is capable of estimating the energy by using the first correlation data D1 on the basis of the light amount of pulsed laser light detected in step S3.

Here, the first correlation data D1 illustrated in FIG. 10 can be created by measuring in advance the light amount and energy of at least a part of pulsed laser light emitted by the laser light source 8. For example, in a state where the laser light source 8 is emitting pulsed laser light, the light amount detecting unit 9 measures the light amount of at least a part of the pulsed laser light while an energy meter or the like measures the energy of the pulsed laser light, and accordingly a relationship between the amount and energy of the part of the pulsed laser light emitted by the laser light source 8 can be acquired. In this case, it is preferable to calculate, for each of the light amount and energy of the part of the pulsed laser light, an average value of a plurality of measurement results. As a result of performing the measurement while changing the input energy of the pulsed laser light, the first correlation data D1 can be created. The amount and energy of the pulsed laser light are in a proportional relationship, as illustrated in FIG. 10.

Figure 11:
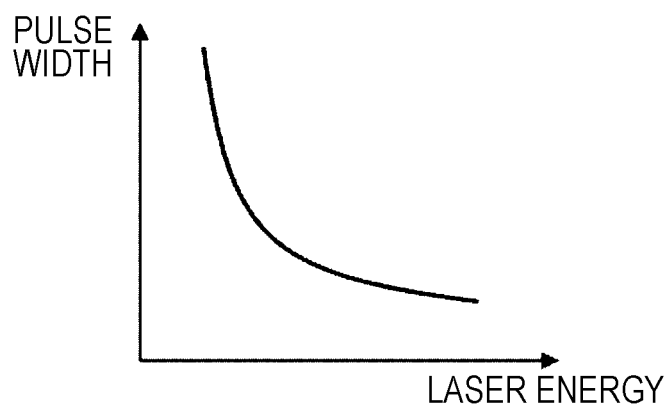
FIG. 11 is a diagram schematically illustrating a correlation between an energy and pulse width of pulsed laser light output from the laser light source.

In the following step S5, the pulse width estimating unit 11 estimates the pulse width of the pulsed laser light on the basis of the energy of the pulsed laser light estimated in step S4 and the second correlation data D2 stored in the correlation data memory 12. Here, the second correlation data D2 is data representing a relationship between the energy and pulse width of pulsed laser light emitted by the laser light source 8 as illustrated in FIG. 11, for example. The pulse width estimating unit 11 is capable of estimating the pulse width by using the second correlation data D2 on the basis of the energy of the pulsed laser light estimated in step S4.

Here, the second correlation data D2 illustrated in FIG. 11 can be created by measuring in advance the energy and pulse width of pulsed laser light emitted by the laser light source 8. For example, in a state where the laser light source 8 is emitting pulsed laser light, an energy meter or the like measures the energy of the pulsed laser light while an oscilloscope or the like measures the pulse width of the pulsed laser light, and accordingly a relationship between the energy and pulse width of the pulsed laser light emitted by the laser light source 8 can be acquired. In this case, it is preferable to calculate, for each of the energy and pulse width of the pulsed laser light, an average value of a plurality of measurement results. As a result of acquiring a relationship between the energy and pulse width of pulsed laser light while changing the input energy of the pulsed laser light, the second correlation data D2 can be created. The energy and pulse width of the pulsed laser light are in an inverse correlation relationship, as illustrated in FIG. 11.

In the following step S6, the photoacoustic signal correcting unit 4 corrects the photoacoustic signal acquired in step S2 on the basis of the energy Ee of the pulsed laser light estimated in step S4, the pulse width We of the pulsed laser light estimated in step S5, and the third correlation data D3 and fourth correlation data D4 stored in the correlation data memory 12.

Figure 12:
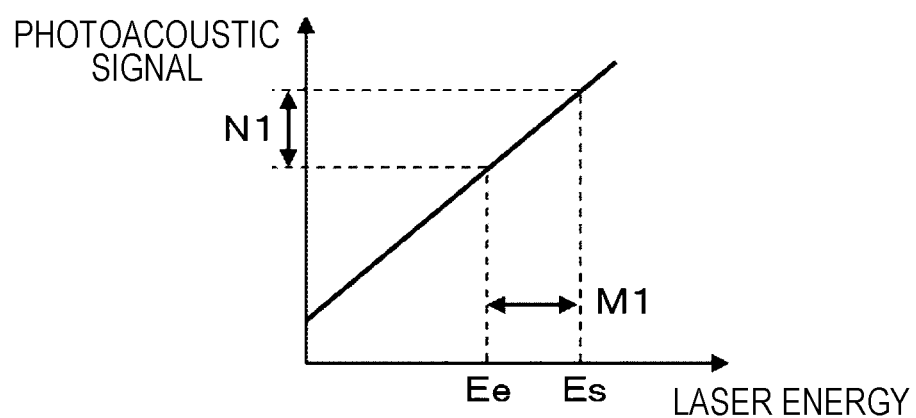
FIG. 12 is a diagram schematically illustrating a correlation between an energy of pulsed laser light output from the laser light source and an intensity of a photoacoustic signal.
Figure 13:
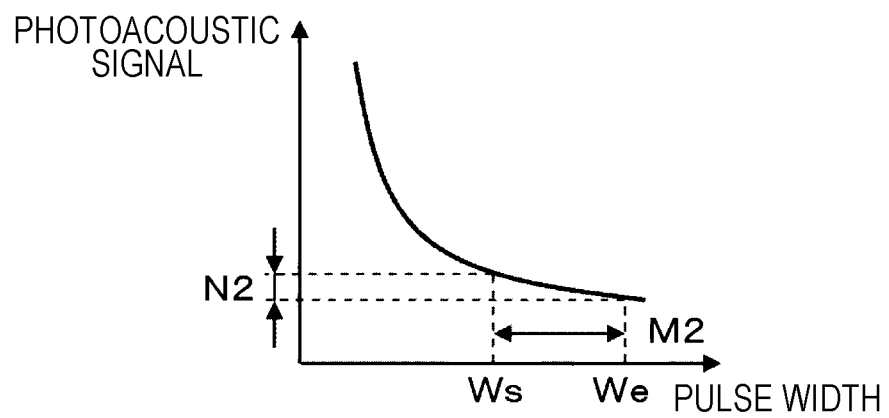
FIG. 13 is a diagram schematically illustrating a correlation between a pulse width of pulsed laser light output from the laser light source and an intensity of a photoacoustic signal.

Here, the third correlation data D3 is data representing a relationship between the energy of pulsed laser light emitted by the laser light source 8 and a photoacoustic signal acquired on the basis of the pulsed laser light as illustrated in FIG. 12, for example. The fourth correlation data D4 is data representing a relationship between the pulse width of pulsed laser light emitted by the laser light source 8 and a photoacoustic signal acquired on the basis of the pulsed laser light as illustrated in FIG. 13, for example. The photoacoustic signal correcting unit 4 is capable of correcting a photoacoustic signal by using the third correlation data D3 and the fourth correlation data D4.

In this case, the first difference calculating unit 41 of the photoacoustic signal correcting unit 4 calculates the first difference M1 between the energy Ee of the pulsed laser light estimated in step S4 and a determined reference energy Es by using the third correlation data D3 illustrated in FIG. 12, and calculates a first correction amount N1 for the intensity of the photoacoustic signal corresponding to the first difference M1. The second difference calculating unit 42 of the photoacoustic signal correcting unit 4 calculates the second difference M2 between the pulse width We of the pulsed laser light estimated in step S5 and a determined reference pulse width Ws by using the fourth correlation data D4 illustrated in FIG. 13, and calculates a second correction amount N2 for the intensity of the photoacoustic signal corresponding to the second difference M2. The correction executing unit 43 of the photoacoustic signal correcting unit 4 collects the photoacoustic signal acquired in step S2 in accordance with the first correction amount N1 calculated by the first difference calculating unit 41 and the second correction amount N2 calculated by the second difference calculating unit 42.

Here, the third correlation data D3 illustrated in FIG. 12 can be created by measuring in advance the energy of pulsed laser light emitted by the laser light source 8 and a photoacoustic signal based on the pulsed laser light.

For example, a system for changing the energy of pulsed laser light while keeping the pulse width constant is constructed. In this system, a certain portion in a phantom is irradiated with pulsed laser light with the probe 2 being in contact with the phantom while an energy meter or the like is measuring the energy of the pulsed laser light, and a photoacoustic signal is acquired on the basis of a photoacoustic wave emitted from the phantom. Accordingly, a relationship between the energy of the pulsed laser light emitted by the laser light source 8 and the photoacoustic signal can be acquired. In this case, it is preferable to calculate, for each of the energy of the pulsed laser light and the photoacoustic signal, an average value of a plurality of measurement results. As a result of performing the measurement while changing the energy of the pulsed laser light, the third correlation data D3 can be created. The measurement may be performed by using the laser light source 8 or may be performed by using a separately constructed laser with the same wavelength.

Here, a phantom is a mockup formed so as to have an acoustic characteristic similar to that of tissue of a human body and is widely known in general.

The fourth correlation data D4 illustrated in FIG. 13 can be created by measuring in advance the pulse width of pulsed laser light emitted by the laser light source 8 and a photoacoustic signal based on the pulsed laser light. For example, a system for changing the pulse with of pulsed laser light while keeping the energy of the pulsed laser light constant is constructed. In this system, a certain portion in a phantom is irradiated with pulsed laser light while an oscilloscope or the like is measuring the pulse width of the pulsed laser light, and a photoacoustic signal is acquired on the basis of a photoacoustic wave emitted from the phantom. Accordingly, a relationship between the pulse width of the pulsed laser light emitted by the laser light source 8 and the photoacoustic signal can be acquired. In this case, it is preferable to calculate, for each of the pulse width of the pulsed laser light and the photoacoustic signal, an average value of a plurality of measurement results. As a result of performing the measurement while changing the pulse width, the fourth correlation data D4 can be created. The measurement may be performed by using the laser light source 8 or may be performed by using a separately constructed laser with the same wavelength.

In the following step S7, the photoacoustic image generating unit 5 generates a photoacoustic image on the basis of the photoacoustic signal corrected in step S6. In this way, the operation of the photoacoustic apparatus 1 according to the first embodiment of the present invention ends.

As described above, in the photoacoustic apparatus 1 according to the first embodiment of the present invention, the light amount of pulsed laser light emitted by the laser light source 8 is actually measured, the energy Ee and the pulse width We of the pulsed laser light are estimated on the basis of an acquired measurement value, and a photoacoustic signal is corrected on the basis of both the energy Ee and the pulse width We. Thus, even if a chronological change in the state of the laser light source 8 causes a change in the energy and pulse width of the pulsed laser light emitted by the laser light source 8, it is possible to reduce an influence of the chronological change in the laser light source 8 on a photoacoustic signal.

In the first embodiment, the correlation data memory 12 may store the first correlation data D1 to the fourth correlation data D4 in any one of a graph format, a table format, an arithmetic expression format, or the like.

The correlation data memory 12 stores, as correlation data that is necessary to correct a photoacoustic signal, four pieces of correlation data: the first correlation data D1 representing a relationship between the light amount and energy of pulsed laser light emitted by the laser light source 8; the second correlation data D2 representing a relationship between the energy and pulse width of the pulsed laser light; the third correlation data D3 representing a relationship between the energy of the pulsed laser light and a photoacoustic signal, and the fourth correlation data D4 representing a relationship between the pulse width of the pulsed laser light and a photoacoustic signal. However, by integrating the four pieces of correlation data, the first correlation data D1 to the fourth correlation data D4, under consideration, it is possible to store one piece of fifth correlation data representing a relationship between the light amount of pulsed laser light and a photoacoustic signal. In this case, the photoacoustic signal correcting unit 4 is capable of correcting the photoacoustic signal acquired from the receiving unit 3 on the basis of only the light amount of pulsed laser light detected by the light amount detecting unit 9 and the fifth correlation data.

In the first embodiment, the light amount detecting unit 9 is disposed outside the laser light source 8, but may be included inside the optical resonator constituting the laser light source 8. Also in this case, the light amount detecting unit 9 can be disposed near the optical path of pulsed laser light emitted by the laser light source 8, and thus the light amount of pulsed laser light can be appropriately detected.

Figure 14:
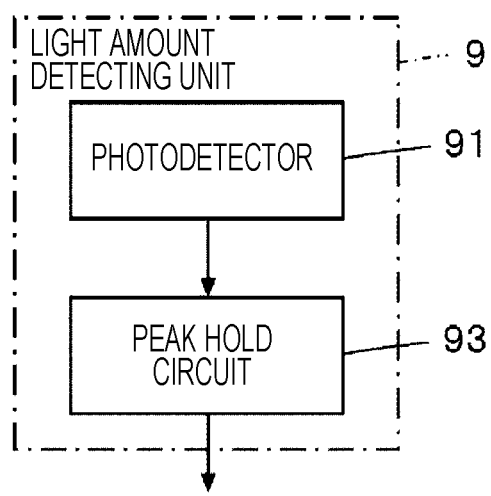
FIG. 14 is a block diagram illustrating an internal configuration of a light amount detecting unit according to a modification example of the first embodiment of the present invention.

In the first embodiment, the light amount detecting unit 9 has the integration circuit 92 and acquires the integral of electric charge of an optical signal detected by the photodetector 91 as the light amount of pulsed laser light. Alternatively, the light amount detecting unit 9 may acquire a crest value, that is, a peak value, of an optical signal as the light amount of pulsed laser light. In this case, the light amount detecting unit 9 may have a peak hold circuit 93 instead of the integration circuit 92 as illustrated in FIG. 14, for example. The peak hold circuit 93 detects a peak value of pulsed laser light and AD converts the peak value into digital data, thereby acquiring the light amount of pulsed laser light.

Second Embodiment

In the first embodiment, the laser light irradiating unit 2B of the probe 2 irradiates the inside of a subject with pulsed laser light having one wavelength. Alternatively, pulsed laser light beams having a respective plurality of wavelengths may be radiated.

Figure 15:
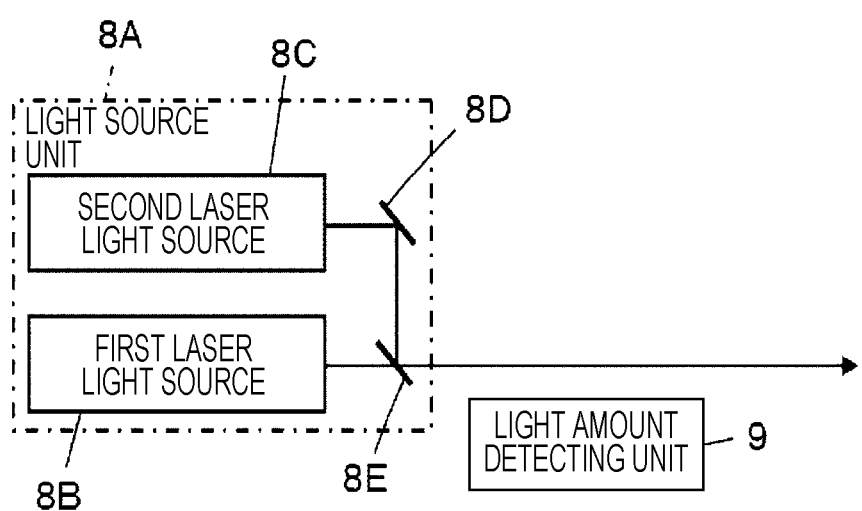
FIG. 15 is a block diagram illustrating an internal configuration of a light source unit according to a second embodiment.

A photoacoustic apparatus according to a second embodiment is different from the photoacoustic apparatus 1 according to the first embodiment in that a light source unit 8A illustrated in FIG. 15 is connected to the laser light irradiating unit 2B of the probe 2, instead of the laser light source 8.

The light source unit 8A has a first laser light source 8B that emits pulsed laser light having a wavelength $\lambda 1$ and a second laser light source 8C that emits pulsed laser light having a wavelength $\lambda 2$, and is configured to emit, using a mirror 8D and a half mirror 8E, the pulsed laser light emitted by the first laser light source 8B and the pulsed laser light emitted by the second laser light source 8C along a common optical path. The light amount detecting unit 9 is disposed near the common optical path of the pulsed laser light beams emitted by the light source unit 8A.

The first laser light source 8B and the second laser light source 8C of the light source unit 8A each have an internal configuration similar to that of the laser light source 8 illustrated in FIG. 2, and emit pulsed laser light having the wavelength $\lambda 1$ and pulsed laser light having the wavelength $\lambda 2$, respectively, the wavelengths $\lambda 1$ and $\lambda 2$ being different from each other, under control by the apparatus control unit 13.

The light amount detecting unit 9 disposed near the common optical path from the light source unit 8A is capable of detecting the light amount of pulsed laser light emitted by the first laser light source 8B and the light amount of pulsed laser light emitted by the second laser light source 8C.

Figure 16:
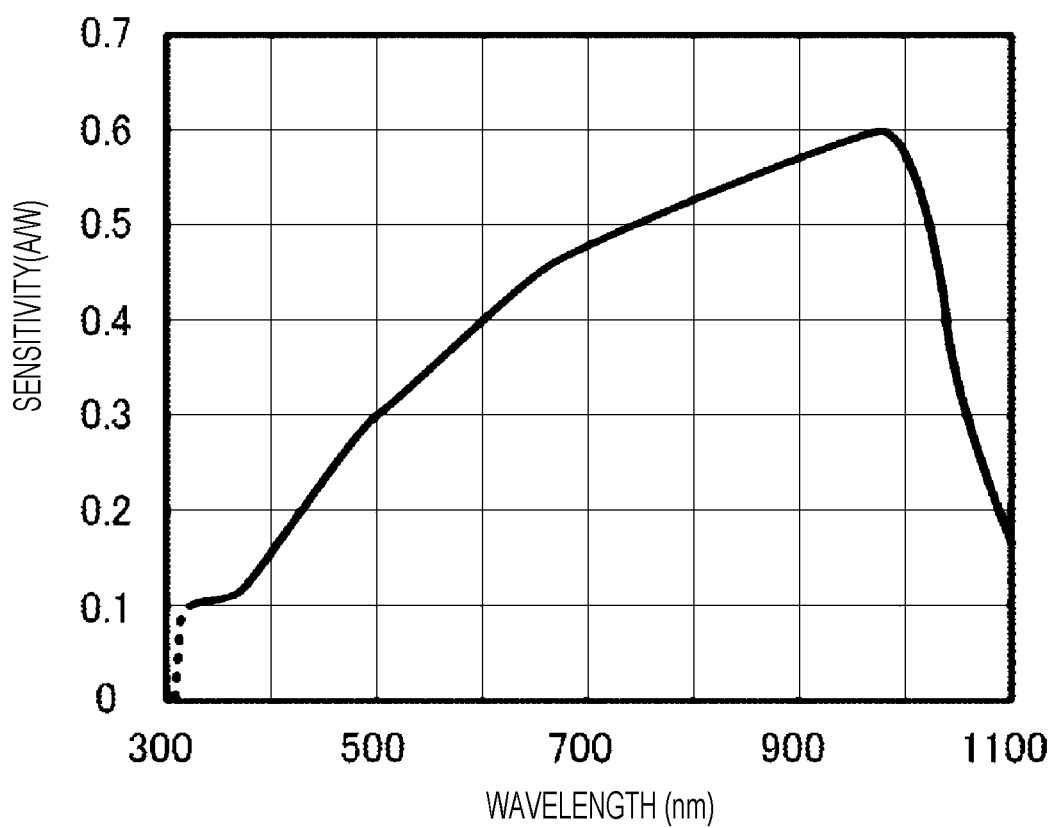
FIG. 16 is a diagram illustrating an example of a sensitivity characteristic of a photodetector.

Here, a phototube such as a photomultiplier tube, a photodiode, a phototransistor, or the like used as the photodetector 91 of the light amount detecting unit 9 has a sensitivity that varies according to the wavelength of laser light to be detected. For example, S1223-01, which is a photodiode made by Hamamatsu Photonics K.K., has a sensitivity characteristic illustrated in FIG. 16, in which the sensitivity varies according to the wavelength of laser light to be detected.

Figure 17:
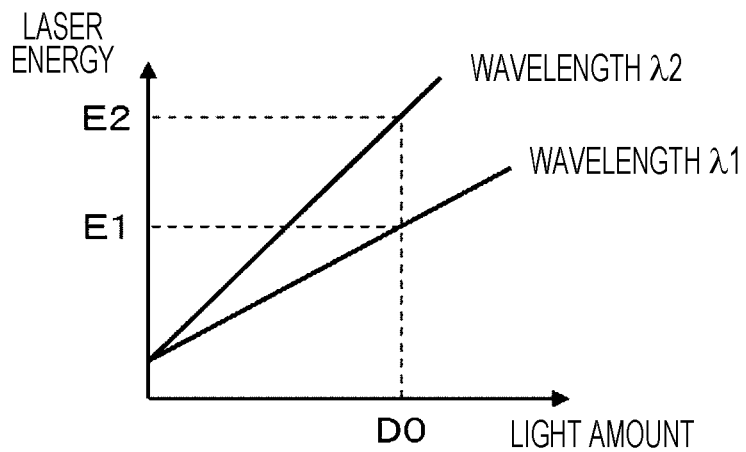
FIG. 17 is a diagram schematically illustrating a correlation between light amount values and energies of pulsed laser light having a wavelength $\lambda 1$ and pulsed laser light having a wavelength $\lambda 2$.

Thus, as illustrated in FIG. 17, the correlation data memory 12 according to the second embodiment stores, as the first correlation data D1, data representing a relationship between the amount and energy of pulsed laser light having the wavelength $\lambda 1$ and data representing a relationship between the amount and energy of pulsed laser light having the wavelength λ2. Furthermore, the correlation data memory 12 stores, for each of the wavelength λ1 and the wavelength λ2, the second correlation data D2, the third correlation data D3, and the fourth correlation data D4, like the first correlation data D1.

The energy estimating unit 10 according to the second embodiment estimates the energy of the pulsed laser light having the wavelength λ1 and the energy of the pulsed laser light having the wavelength λ2 on the basis of the first correlation data D1 about the pulsed laser light having the wavelength λ1 and the pulsed laser light having the wavelength λ2 stored in the correlation data memory 12, and the amount of the pulsed laser light having the wavelength λ1 and the amount of the pulsed laser light having the wavelength λ2 detected by the light amount detecting unit 9. For example, the energy estimating unit 10 estimates an energy E1 for a light amount D0 of the pulsed laser light having the wavelength λ1 and estimates an energy E2 for a light amount D0 of the pulsed laser light having the wavelength λ2.

The pulse width estimating unit 11 according to the second embodiment estimates the pulse width of the pulsed laser light having the wavelength λ1 and the pulse with of the pulsed laser light having the wavelength λ2 on the basis of the second correlation data D2 about the pulsed laser light having the wavelength λ1 and the pulsed laser light having the wavelength λ2 stored in the correlation data memory 12, and the energy of the pulsed laser light having the wavelength λ1 and the energy of the pulsed laser light having the wavelength λ2 estimated by the energy estimating unit 10.

The photoacoustic signal correcting unit 4 according to the second embodiment corrects a photoacoustic signal based on the pulsed laser light having the wavelength λ1 and a photoacoustic signal based on the pulsed laser light having the wavelength λ2 on the basis of the third correlation data D3 and the fourth correlation data D4 about the pulsed laser light having the wavelength λ1 and the pulsed laser light having the wavelength λ2 stored in the correlation data memory 12, the energy of the pulsed laser light having the wavelength λ1 and the energy of the pulsed laser light having the wavelength λ2 estimated by the energy estimating unit 10, and the pulse width of the pulsed laser light having the wavelength λ1 and the pulse width of the pulsed laser light having the wavelength λ2 estimated by the pulse width estimating unit 11.

In this case, the first difference calculating unit 41 of the photoacoustic signal correcting unit 4 calculates the first difference M1 and the first correction amount N1 for each of the pulsed laser light having the wavelength λ1 and the pulsed laser light having the wavelength λ2, and the second difference calculating unit 42 of the photoacoustic signal correcting unit 4 calculates the second difference M2 and the second correction amount N2 for each of the pulsed laser light having the wavelength λ1 and the pulsed laser light having the wavelength λ2. The correction executing unit 43 of the photoacoustic signal correcting unit 4 performs correction based on the first correction amount N1 and the second correction amount N2 on the photoacoustic signal T1 acquired on the basis of the pulsed laser light having the wavelength λ1 and the photoacoustic signal T1 acquired on the basis of the pulsed laser light having the wavelength λ2.

As described above, in the photoacoustic apparatus according to the second embodiment, even in a case where the laser light irradiating unit 2B of the probe 2 irradiates the inside of a subject with two types of pulsed laser light beams having the wavelengths λ1 and λ2 different from each other, the amounts of the pulsed laser light beams having the wavelengths λ1 and λ2 are measured as appropriate to estimate the energies and pulse widths thereof, and photoacoustic signals corresponding to the respective wavelengths λ1 and λ2 are corrected. Thus, it is possible to reduce an influence of chronological changes in the first laser light source 8B and the second laser light source 8C of the light source unit 8A on the photoacoustic signals.

In the second embodiment, two types of pulsed laser light beams having the wavelengths λ1 and λ2 different from each other are emitted by the first laser light source 8B and the second laser light source 8C of the light source unit 8A, respectively. Alternatively, the two types of pulsed laser light beams having the wavelengths λ1 and λ2 different from each other may be emitted by one laser light source. For example, a laser light source that emits pulsed laser light including a plurality of specific wavelengths is used as one laser light source, and a wavelength selective filter that is not illustrated is provided in the laser light source. Accordingly, the wavelengths λ1 and λ2 of the pulsed laser light emitted by the laser light source can be appropriately switched therebetween.

Here, the wavelength selective filter is a filter that allows only pulsed laser light having the specific wavelength λ1 or λ2 to pass therethrough and that blocks pulsed laser light having the other wavelengths. In such a case where one laser light source emits pulsed laser light beams having the two wavelengths λ1 and λ2, the operation time of the laser light source is longer than in the case of using two laser light sources, and thus changes in the energy and pulse width of pulsed laser light caused by elapse of time may be large. In the photoacoustic apparatus according to the second embodiment, correction of a photoacoustic signal based on the energy and pulse width is performed for each of pulsed laser light beams having two different wavelengths λ1 and λ2, and thus it is possible to reduce an influence of a chronological change in the laser light source 8 on a photoacoustic signal and to acquire a photoacoustic image with high accuracy.

In the second embodiment, the amounts of two types of pulsed laser light beams having the two wavelengths λ1 and λ2 are detected by the light amount detecting unit 9 including one photodetector 91. Alternatively, two different photodetectors may be used for the two types of pulsed laser light beams having the wavelengths λ1 and λ2 to detect the amounts of two types of pulsed laser light beams. For example, the light amount detecting unit 9 illustrated in FIG. 4 may have the photodetector 91 having the sensitivity characteristic illustrated in FIG. 16 and a second photodetector having the sensitivity characteristic illustrated in FIG. 18 and not illustrated, and the photodetector 91 and the second photodetector may be connected to the integration circuit 92. Accordingly, the amounts of two types of pulsed laser light beams can be detected by using the two different photodetectors for the two types of pulsed laser light beams having the wavelengths λ1 and λ2.

Figure 18:
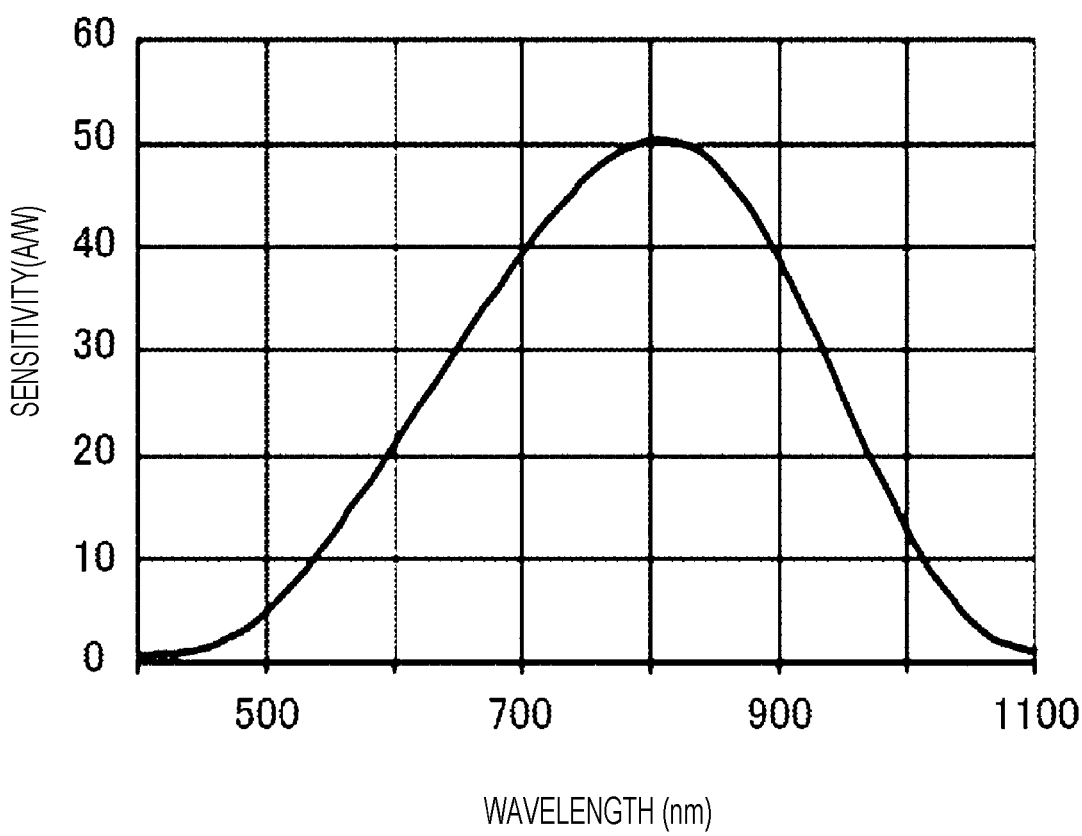
FIG. 18 is a diagram illustrating another example of a sensitivity characteristic of a photodetector.

The sensitivity characteristic illustrated in FIG. 18 is the sensitivity characteristic of APD15-8-150, which is a photodiode made by OSI Optoelectronics.

In the photoacoustic apparatus according to the second embodiment, the laser light irradiating unit 2B of the probe 2 irradiates the inside of a subject with pulsed laser light having the wavelength λ1 and pulsed laser light having the wavelength λ2. Alternatively, the laser light irradiating unit 2B may irradiate the inside of a subject with a plurality of, that is, three or more types of, pulsed laser light beams having wavelengths different from each other. For example, the photoacoustic apparatus 1 illustrated in FIG. 1 may be provided with a plurality of laser light sources, that is, three or more laser light sources that emit respective pulsed laser light beams having wavelengths different from each other. A laser light source that emits pulsed laser light including specific three or more types of wavelengths may be used as the one laser light source 8, and the laser light source 8 may be provided with a wavelength selective filter.

In this case, the correlation data memory 12 stores, for each of the plurality of wavelengths, the first correlation data D1, the second correlation data D2, the third correlation data D3, and the fourth correlation data D4. The energy estimating unit 10 estimates the energy Ee of pulsed laser light on the basis of the light amount of pulsed laser light detected by the light amount detecting unit 9 for each of the plurality of wavelengths and the first correlation data D1 stored in the correlation data memory 12 for each of the plurality of wavelengths. The pulse width estimating unit 11 estimates the pulse width We of the pulsed laser light on the basis of the energy Ee of the pulsed laser light estimated by the energy estimating unit 10 for each of the plurality of wavelengths and the second correlation data D2 stored in the correlation data memory 12 for each of the plurality of wavelengths.

Furthermore, the photoacoustic signal correcting unit 4 corrects photoacoustic signals acquired on the basis of the pulsed laser light beams having the respective plurality of wavelengths, on the basis of the energy Ee and pulse width We estimated for each of the plurality of wavelengths by the energy estimating unit 10 and the pulse width estimating unit 11, and the third correlation data D3 and the fourth correlation data D4 stored in the correlation data memory 12 for each of the plurality of wavelengths.

In such a case where the inside of a subject is irradiated with a plurality of pulsed laser light beams, that is, three or more types of pulsed laser light beams, having wavelengths different from each other, the photoacoustic apparatus according to the second embodiment of the present invention is capable of reducing an influence of chronological changes in the respective laser light sources on photoacoustic signals and acquiring a photoacoustic image with high accuracy.

In general, substance in the living body of a subject has an absorptance for pulsed laser light that varies according to the wavelength range of the pulsed laser light applied thereto. Thus, as a result of setting the wavelength ranges of the wavelengths $\lambda 1$ and $\lambda 2$ of the pulsed laser light beams applied to the inside of the subject in the second embodiment in accordance with the absorptance of specific substance in the living body, it is possible to generate an image representing a distribution of the substance in the living body, such as an oxygen saturation distribution image. For example, the wavelength $\lambda 1$ of pulsed laser light emitted by the first laser light source 8B is set to be in a wavelength range in which the absorptance of oxyhemoglobin is substantially equal to the absorptance of deoxyhemoglobin, the wavelength $\lambda 2$ of pulsed laser light emitted by the second laser light source 8C is set to be in a wavelength range in which the absorptance of oxyhemoglobin is significantly different from the absorptance of deoxyhemoglobin, and a corrected photoacoustic signal based on the pulsed laser light having the wavelength $\lambda 1$ and a corrected photoacoustic signal based on the pulsed laser light having the wavelength $\lambda 2$ are used. Accordingly, an image representing an oxygen saturation distribution in the subject can be acquired. In this case, for example, the wavelength $\lambda 1$ is set to 1064 nm and the wavelength $\lambda 2$ is set to 756 nm, and thereby an image representing an oxygen saturation distribution in the subject can be acquired.

Similarly, as a result of setting the wavelengths $\lambda 1$ and $\lambda 2$ of pulsed laser light beams applied to the inside of the subject to be in a wavelength range in which the absorptance of specific substance in the living body is high, it is possible to acquire, using the photoacoustic apparatus according to the second embodiment, an image representing a distribution of lipid in the subject, an image representing a distribution of melanin, an image representing a distribution of coloring pigment introduced into the subject, such as indocyanine green or methylene blue, an image representing a distribution of an organism layer region, such as blood vessels, lymph vessels, or nerves, or the like. For example, to acquire an image representing a distribution of lipid in the subject, the wavelength $\lambda 1$ may be set to 920 nm and the wavelength $\lambda 2$ may be set to 1065 nm.

Third Embodiment

A typical laser light source chronologically changes, for example, degrades, by continuously emitting pulsed laser light. As a result, the energy of pulsed laser light emitted by the laser light source may decrease and the pulse width may increase. Such a chronological change in the laser light source causes a significant change in the energy and pulse width of pulsed laser light emitted by the laser light source. Thus, a photoacoustic wave having a sufficient intensity and frequency is not acquired in some cases when substance in the living body of a subject is irradiated with pulsed laser light emitted by the laser light source.

Figure 19:
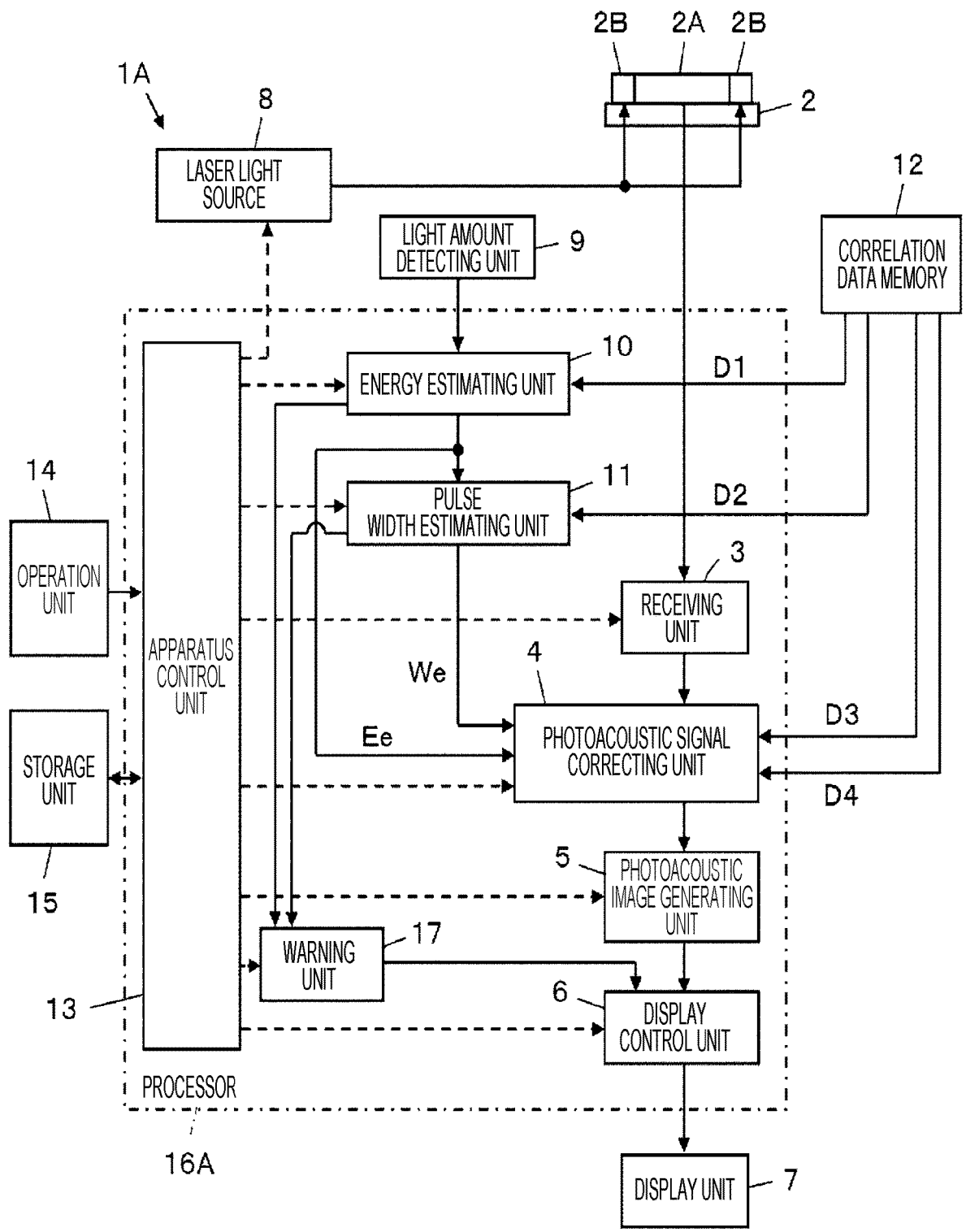
FIG. 19 is a block diagram illustrating the configuration of a photoacoustic apparatus according to a third embodiment of the present invention.

Accordingly, it is possible to cause a user to recognize that the energy and pulse width of pulsed laser light emitted by a laser light source are significantly changing in accordance with a chronological change in the laser light source. As illustrated in FIG. 19, a photoacoustic apparatus 1A according to a third embodiment is different from the photoacoustic apparatus 1 according to the first embodiment illustrated in FIG. 1 in that a warning unit 17 is provided. The warning unit 17 is connected to the energy estimating unit 10 and the pulse width estimating unit 11, and is also connected to the display control unit 6 and the apparatus control unit 13.

Furthermore, the receiving unit 3, the photoacoustic signal correcting unit 4, the photoacoustic image generating unit 5, the display control unit 6, the energy estimating unit 10, the pulse width estimating unit 11, the apparatus control unit 13, and the warning unit 17 constitute a processor 16A.

The warning unit 17 of the processor 16A displays a warning on the display unit 7 via the display control unit 6 in a case where the amount of temporal change in the energy Ee of pulsed laser light estimated by the energy estimating unit 10 exceeds a determined energy upper limit value, and also displays a warning on the display unit 7 via the display control unit 6 in a case where the amount of temporal change in the pulse width We of pulsed laser light estimated by the pulse width estimating unit 11 exceeds a determined pulse width upper limit value. In this case, the warning unit 17 constantly monitors the amount of temporal change in the energy Ee of pulsed laser light estimated by the energy estimating unit 10 and the amount of temporal change in the pulse width We of pulsed laser light estimated by the pulse width estimating unit 11.

The warning made by the warning unit 17 is not limited to be displayed on the display unit 7. For example, a warning may be made using a sound.

From the above, the warning unit 17 enables the user to immediately recognize that the intensity of an acquired photoacoustic signal is decreasing because at least one of the energy Ee of pulsed laser light estimated by the energy estimating unit 10 or the pulse width We of pulsed laser light estimated by the pulse width estimating unit 11 is significantly changing due to a chronological change in the laser light source 8.

Fourth Embodiment

In a case where the energy of pulsed laser light emitted by the laser light source 8 has a value out of a determined energy guarantee range or in a case where the pulse width of pulsed laser light has a value out of a determined pulse width guarantee range, there is a possibility that abnormality has occurred in the laser light source 8 for some reasons. In this case, it is not possible to acquire an accurate photoacoustic signal for generating a photoacoustic image, and thus emission of pulsed laser light by the laser light source 8 can be stopped.

Figure 20:
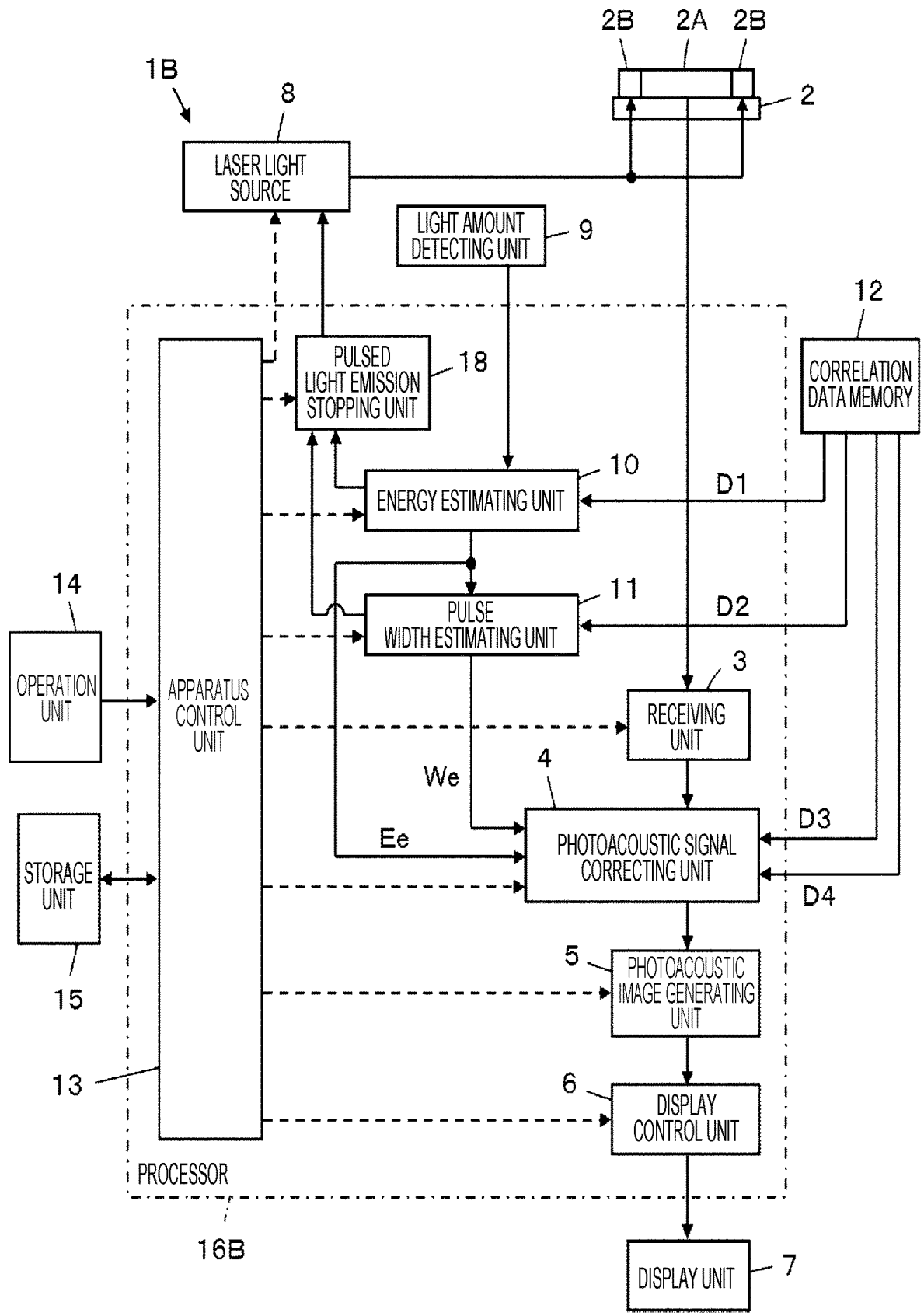
FIG. 20 is a block diagram illustrating the configuration of a photoacoustic apparatus according to a fourth embodiment of the present invention.

As illustrated in FIG. 20, a photoacoustic apparatus 1B according to a fourth embodiment is different from the photoacoustic apparatus 1 according to the first embodiment illustrated in FIG. 1 in that a pulsed light emission stopping unit 18 is provided. The pulsed light emission stopping unit 18 is connected to the energy estimating unit 10 and the pulse width estimating unit 11, and is also connected to the laser light source 8. In addition, the pulsed light emission stopping unit 18 is connected to the apparatus control unit 13.

Furthermore, the receiving unit 3, the photoacoustic signal correcting unit 4, the photoacoustic image generating unit 5, the display control unit 6, the energy estimating unit 10, the pulse width estimating unit 11, the apparatus control unit 13, and the pulsed light emission stopping unit 18 constitute a processor 16B.

The pulsed light emission stopping unit 18 of the processor 16B stops emission of pulsed laser light by the laser light source 8 in a case where the energy Ee of pulsed laser light estimated by the energy estimating unit 10 is out of a determined energy guarantee range or in a case where the pulse width We of pulsed laser light estimated by the pulse width estimating unit 11 is out of a determined pulse width guarantee range.

In this way, emission of pulsed laser light from the laser light source 8 can be stopped by the pulsed light emission stopping unit 18 in a case where the energy of the pulsed laser light has a value out of the determined energy guarantee range or in a case where the pulse width of the pulsed laser light has a value out of the determined pulse width guarantee range, and thus a photoacoustic image can be generated safely and accurately.

From the above description, the photoacoustic apparatus described in the following appendix 1 can be grasped.

APPENDIX 1

A photoacoustic apparatus including:
a laser light source that emits pulsed laser light;
a probe that irradiates an inside of a subject with the pulsed laser light to cause a photoacoustic wave to be emitted from tissue of the subject and that receives the photoacoustic wave emitted from the tissue of the subject;
a light amount detecting circuit that detects a light amount of the pulsed laser light emitted by the laser light source;
a correlation data memory that stores first correlation data and second correlation data, the first correlation data representing a relationship between a light amount detected by the light amount detecting circuit and an energy of the pulsed laser light, the second correlation data representing a relationship between an energy of the pulsed laser light and a pulse width of the pulsed laser light; and
a processor,
wherein the processor
acquires a photoacoustic signal from the probe,
estimates an energy of the pulsed laser light by using the first correlation data on the basis of the light amount detected by the light amount detecting circuit,
estimates a pulse width of the pulsed laser light by using the second correlation data on the basis of the estimated energy of the pulsed laser light,
corrects the acquired photoacoustic signal on the basis of both a first difference between the estimated energy of the pulsed laser light and a determined reference energy and a second difference between the estimated pulse width of the pulsed laser light and a determined reference pulse width, and
generates a photoacoustic image from the corrected photoacoustic signal.

REFERENCE SIGNS LIST 1, 1A, 1B photoacoustic apparatus
2 probe
2A array transducer
2B laser light irradiating unit
3 receiving unit
4 photoacoustic signal correcting unit
5 photoacoustic image generating unit
6 display control unit
7 display unit
8 laser light source
8A light source unit
8B first laser light source
8C second laser light source
8D mirror
8E half mirror
9 light amount detecting unit
10 energy estimating unit
11 pulse width estimating unit
12 correlation data memory
13 apparatus control unit
14 operation unit
15 storage unit
16, 16A, 16B processor
17 warning unit
18 pulsed light emission stopping unit
31 amplifying unit
32 AD converter
41 first difference calculating unit
42 second difference calculating unit
43 correction executing unit
51 signal processing unit
52 DSC
53 image processing unit
81 laser rod
82 excitation light source
83, 84 mirror
85 polarizer
86 Q switch
91 photodetector
92 integration circuit 93 peak hold circuit
D0 light amount
D1 first correlation data
D2 second correlation data
D3 third correlation data
D4 fourth correlation data
Ee, E1, E2 energy
Ed, Wd variation
Es reference energy
M1 first difference
M2 second difference
N1 first correction amount
N2 second correction amount
T1, T2 photoacoustic signal
We pulse width
Ws reference pulse width
λ1, λ2 wavelength

What is claimed is:

1. A photoacoustic apparatus comprising:
a laser light source configured to emit pulsed laser light;
a probe configured to irradiate an inside of a subject with the pulsed laser light to cause a photoacoustic wave to be emitted from tissue of the subject and receive the photoacoustic wave emitted from the tissue of the subject;
a light amount detecting circuit configured to detect a light amount of the pulsed laser light emitted by the laser light source;
a correlation data memory configured to store first correlation data and second correlation data, the first correlation data representing a relationship between the light amount detected by the light amount detecting circuit and an energy of the pulsed laser light, the second correlation data representing a relationship between the energy of the pulsed laser light and a pulse width of the pulsed laser light; and
a processor configured to acquire a photoacoustic signal from the probe;
estimate the energy of the pulsed laser light by using the first correlation data on the basis of the light amount detected by the light amount detecting circuit;
estimate a pulse width of the pulsed laser light by using the second correlation data on the basis of the estimated energy of the pulsed laser light;
correct the photoacoustic signal on the basis of both a first difference between the estimated energy of the pulsed laser light and a determined reference energy and a second difference between the estimated pulse width of the pulsed laser light and a determined reference pulse width; and
generate a photoacoustic image from the corrected photoacoustic signal corrected.

2. The photoacoustic apparatus according to claim 1, wherein the processor is further configured to calculate the first difference on the basis of the estimated energy of the pulsed laser light and the determined reference energy,
calculate the second difference on the basis of the estimated pulse width of the pulsed laser light and the determined reference pulse width,
correct the photoacoustic signal in accordance with the first difference, and
correct the photoacoustic signal in accordance with the second difference.

3. The photoacoustic apparatus according to claim 2, wherein
the correlation data memory is further configured to store third correlation data and fourth correlation data, the third correlation data representing a relationship between the energy of the pulsed laser light and the photoacoustic signal, the fourth correlation data representing a relationship between the pulse width of the pulsed laser light and the photoacoustic signal acquired by the photoacoustic signal acquiring unit, and
the processor is further configured to
correct the photoacoustic signal on the basis of the first difference and the third correlation data, and
correct the photoacoustic signal on the basis of the second difference and the fourth correlation data.

4. The photoacoustic apparatus according to claim 1, wherein the laser light source is further configured to emit pulsed laser light beams having a respective plurality of wavelengths,
the processor is further configured to acquire, for each wavelength, the photoacoustic signal,
the correlation data memory is further configured to store, for each wavelength, the first correlation data and the second correlation data corresponding to the wavelength, and
the processor is further configured to
estimate, for each wavelength, an energy of the pulsed laser light beam,
the pulse width estimating unit estimates, estimate, for each wavelength, a pulse width of the pulsed laser light beam,
correct, for each wavelength, the photoacoustic signal, and
generate, for each wavelength, the photoacoustic image.

5. The photoacoustic apparatus according to claim 2, wherein the laser light source is further configured to emit pulsed laser light beams having a respective plurality of wavelengths,
the processor is further configured to acquire, for each wavelength, the photoacoustic signal,
the correlation data memory is further configured to store, for each wavelength, the first correlation data and the second correlation data corresponding to the wavelength, and
the processor is further configured to
estimate, for each wavelength, an energy of the pulsed laser light beam,
estimate, for each wavelength, a pulse width of the pulsed laser light beam,
correct, for each wavelength, the photoacoustic signal, and
generate, for each wavelength, the photoacoustic image.

6. The photoacoustic apparatus according to claim 3, wherein
the laser light source is further configured to emit pulsed laser light beams having a respective plurality of wavelengths,
the processor is further configured to acquire, for each wavelength, the photoacoustic signal,
the correlation data memory is further configured to store, for each wavelength, the first correlation data and the second correlation data corresponding to the wavelength, and
the processor is further configured to
estimate, for each wavelength, an energy of the pulsed laser light beam,
estimate, for each wavelength, a pulse width of the pulsed laser light beam,
correct, for each wavelength, the photoacoustic signal, and
generate, for each wavelength, the photoacoustic image.

7. The photoacoustic apparatus according to claim 4, wherein the light amount detecting circuit comprises a single light amount detecting circuit configured to detect amounts of the pulsed laser light beams having the respective plurality of wavelengths.

8. The photoacoustic apparatus according to claim 5, wherein the light amount detecting circuit comprises a single light amount detecting circuit configured to detect amounts of the pulsed laser light beams having the respective plurality of wavelengths.

9. The photoacoustic apparatus according to claim 6, wherein the light amount detecting circuit comprises a single light amount detecting circuit configured to detect amounts of the pulsed laser light beams having the respective plurality of wavelengths.

10. The photoacoustic apparatus according to claim 4, wherein the light amount detecting circuit comprises a plurality of light amount detecting circuits each configured to detect an amount of one of the pulsed laser light beams having the respective plurality of wavelengths.

11. The photoacoustic apparatus according to claim 5, wherein the light amount detecting circuit comprises a plurality of light amount detecting circuits each configured to detect an amount of one of the pulsed laser light beams having the respective plurality of wavelengths.

12. The photoacoustic apparatus according to claim 4, wherein
the processor is further configured to generate an image about a characteristic distribution in a living body or an image about a living tissue distribution.

13. The photoacoustic apparatus according to claim 1, wherein the light amount detecting circuit includes a photodetector and either an integration circuit or a peak hold circuit, the integration circuit computing an integral of electric charge of an optical signal detected by the photodetector, the peak hold circuit measuring a crest value of the optical signal.

14. The photoacoustic apparatus according to claim 13, wherein the photodetector is formed of any one of a photodiode, a phototransistor, or a phototube.

15. The photoacoustic apparatus according to claim 13, wherein the photodetector is further configured to detect either a part of light branched off from an optical path of the pulsed laser light emitted by the laser light source or scattered light of the pulsed laser light emitted by the laser light source.

16. The photoacoustic apparatus according to claim 13, wherein the photodetector is disposed inside a resonator of the laser light source.

17. The photoacoustic apparatus according to claim 1, wherein
the processor is further configured to
monitor at least one of an amount of temporal change in the estimated energy of the pulsed laser light or an amount of temporal change in the estimated pulse width of the pulsed laser light, and
issue a warning in a case where the amount of temporal change that is being monitored exceeds an upper limit value determined for the estimated energy of the pulsed laser light or an upper limit value determined for the estimated pulse width of the pulsed laser light.

18. The photoacoustic apparatus according to claim 1, wherein
the processor is further configured to stop emission of the pulsed laser light from the laser light source in a case where at least one of the estimated energy of the pulsed laser light or the estimated pulse width of the pulsed laser light is out of a guarantee range determined for the estimated energy of the pulsed laser light or a guarantee range determined for the estimated pulse width of the pulsed laser light.

19. A method for controlling a photoacoustic apparatus, comprising:
irradiating an inside of a subject with pulsed laser light emitted by a laser light source to cause a photoacoustic wave to be emitted from tissue of the subject;
receiving the photoacoustic wave emitted from the tissue of the subject and acquiring a photoacoustic signal;
detecting a light amount of the pulsed laser light emitted by the laser light source;
estimating an energy of the pulsed laser light by using first correlation data on the basis of the detected light amount of the pulsed laser light, the first correlation data representing a relationship between a light amount of the pulsed laser light emitted by the laser light source and an energy of the pulsed laser light;
estimating a pulse width of the pulsed laser light by using second correlation data on the basis of the estimated energy of the pulsed laser light, the second correlation data representing a relationship between the energy of the pulsed laser light and the pulse width of the pulsed laser light;
correcting the photoacoustic signal on the basis of both a first difference between the estimated energy of the pulsed laser light and a determined reference energy and a second difference between the estimated pulse width of the pulsed laser light and a determined reference pulse width; and
generating a photoacoustic image from the corrected photoacoustic signal.

* * * * *